(12) United States Patent
Isola et al.

(10) Patent No.: US 11,395,926 B2
(45) Date of Patent: Jul. 26, 2022

(54) TREATMENT PLAN GENERATION FOR RADIATION THERAPY TREATMENT

(71) Applicant: KONINKLIJKE PHILIPS N.V., Eindhoven (NL)

(72) Inventors: Alfonso Agatino Isola, Eindhoven (NL); Christoph Neukirchen, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 400 days.

(21) Appl. No.: 16/618,417

(22) PCT Filed: Jun. 7, 2018

(86) PCT No.: PCT/EP2018/065096
§ 371 (c)(1),
(2) Date: Dec. 2, 2019

(87) PCT Pub. No.: WO2018/224623
PCT Pub. Date: Dec. 13, 2018

(65) Prior Publication Data
US 2021/0138264 A1    May 13, 2021

(30) Foreign Application Priority Data

Jun. 8, 2017 (EP) ..................... 17174939

(51) Int. Cl.
*A61N 5/10* (2006.01)
*G16H 20/40* (2018.01)

(52) U.S. Cl.
CPC ......... *A61N 5/1031* (2013.01); *A61N 5/1001* (2013.01); *G16H 20/40* (2018.01)

(58) Field of Classification Search
None
See application file for complete search history.

(56) References Cited

U.S. PATENT DOCUMENTS 7,529,339 B2    5/2009    Goldman
2012/0136194 A1    5/2012    Zhang
(Continued)

FOREIGN PATENT DOCUMENTS

| CN | 104645500 A | 5/2015 |
| EP | 1511535 B1 | 12/2010 |
| EP | 2260902 A1 | 12/2010 |

OTHER PUBLICATIONS

International Search Report and Written Opinion for PCT/EP2018/065096, dated Jul. 5, 2018.
(Continued)

*Primary Examiner* — Hoon K Song

(57) ABSTRACT

The invention relates to a system for planning a radiation therapy treatment. The system obtains a first treatment plan generated in accordance with values of parameters quantifying an amount of radiation provided by radiation components, obtains an instruction to change a radiation dose delivered to at least one volume element, and directly calculates, for each of the radiation components, a change of the amount of radiation provided by the radiation component based on the instruction and based on the contribution of the radiation component to the radiation dose delivered to the at least one volume element. In order to observe upper and/or lower thresholds of the parameter values, the updated parameter values are calculated by iteratively adding the determined changes to the parameter values until a parameter value reaches the threshold or until the desired dose change is realized.

13 Claims, 3 Drawing Sheets

(56) References Cited

U.S. PATENT DOCUMENTS

| | | |
|---|---|---|
| 2013/0102830 A1 | 4/2013 | Otto |
| 2014/0018607 A1 | 1/2014 | Maier |
| 2017/0028221 A1 | 2/2017 | Kontaxis |
| 2017/0157423 A1* | 6/2017 | Bokrantz ............. A61N 5/1047 |
| 2018/0318605 A1* | 11/2018 | Da Silva Rodrigues .................... A61N 5/1038 |
| 2020/0261744 A1* | 8/2020 | Kumar ................. A61N 5/1077 |
| 2021/0038913 A1* | 2/2021 | Liu ...................... A61N 5/1081 |

OTHER PUBLICATIONS

Cotrutz, Christian et al "IMRT Dose Shaping with Regionally Variable Penalty Scheme" Medical Physics, vol. 30, No. 4, 2003.

Poulin, E. et al, "Adaptation of the CVT Algorithm for Catheter Optimization in High Dose Rate Brachytherapy", Medical Physics, (2013), vol. 40 (11) 111724. Abstract Only.

Lessard, E. et al, "Inverse Planning Anatomy-Based Dose Optimization for HDR-Brachytherapy of the Prostate using Fast Simulated Annealing Algorithm and Dedicated Objective Function", Medical Physics, (2001), vol. 28(5), pp. 773-779. Abstract Only.

De Battisti, M. Borat et al "Adaptive Planning Strategy for High Dose Rate Prostate Brachtherapy—a Simulation Study on Needle Positioning Errors", Physics in Medicine & Biology, vol. 61, pp. 2177-2195, 2016.

* cited by examiner

TREATMENT PLAN GENERATION FOR RADIATION THERAPY TREATMENT

CROSS-REFERENCE TO PRIOR APPLICATIONS

This application is the U.S. National Phase application under 35 U.S.C. § 371 of International Application No. PCT/EP2018/065096, filed on Jun. 7, 2018, which claims the benefit of European Patent Application No. 17174939.3, filed on Jun. 8, 2017. These applications are hereby incorporated by reference herein.

FIELD OF THE INVENTION

The invention generally relates to a user-guided planning of a radiation therapy treatment. More specifically, the invention relates to a system, a method and a computer program for generating a treatment plan for a radiation therapy treatment of a target structure within a region of a patient body.

BACKGROUND OF THE INVENTION

In radiation therapy, target structures, such as tumors, within patients' bodies are treated by means radioactive or electromagnetic radiation or ultrasound waves in order to control growth of or kill cancer cells. At the same time, the treatment is delivered in such a way that the radiation or thermal dose delivered to surrounding healthy structures, which are usually also referred to as organs at risk (OARs), is as low as possible.

One exemplary radiation therapy procedure is the so called temporary brachytherapy in which an applicator is used to place one or more radioactive radiation source(s) within the treatment region for a defined short time interval (usually referred to as dwell time) in order to apply a defined radiation dose particularly to the tumor cells. A further radiation therapy procedure is external beam radiation therapy in which a focused and specifically shaped external radiation beam is directed to the target structure. Further examples of radiation therapy procedures comprise radio frequency (RF) and microwave treatments and laser ablation. Moreover, the term radiation therapy as used herein also encompasses other ablation therapy modalities such as particular high intensity focused ultrasound (HIFU).

The treatment parameters for controlling the treatment are defined in a treatment plan, which is generated in a planning system. In order to determine the treatment plan, a so-called inverse planning procedure may be carried out. In such a procedure, the target structure and surrounding OARs are identified and treatment goals are specified. Such treatment goals include soft constraints which may specify requirements for the dose delivered to certain regions of the patient, which should be fulfilled, and/or hard constraints for the doses delivered to certain regions, which must be fulfilled. Then, an optimization process is carried out to find the treatment plan which fulfills the specified treatment goals.

According to one approach for finding the final treatment plan, an operator-guided iterative optimization procedure is carried out in which a pre-optimized treatment plan is further optimized in several cycles. In this procedure, an automatic optimization of the treatment plan is made in each optimization cycles and after each optimization cycle the operator of the planning system (typically a physician) may review the treatment plan as calculated in the respective cycle in order to check whether he/she is satisfied with the dose distribution resulting from the respective treatment plan. If this is not the case, the operator may make modifications to the optimization problem to achieve a desired dose distribution, and the next automatic optimization of the treatment plan may be carried out on the basis of the modified optimization problem.

The automatic optimization of the treatment plan involves solving an optimization problem, which is formulated on the basis of the soft and hard constraints. In a typical planning system, the optimization problem corresponds to the minimization of a cost function which is a weighted sum of individual objective functions, where each individual objective function represents one soft constraint. In addition, it has to be ensured that the hard constraints are satisfied. Typical objective functions relate to a minimum dose to be delivered to a certain region of the target structure and to a maximum dose to be delivered to an OAR, where the corresponding objective functions are configured such that they have a (global) minimum when these dose requirements are fulfilled.

In order to adapt the treatment plan generated in one optimization cycle in such a system, the dose requirements themselves can generally not be modified, since these requirements are usually set to correspond to the desired dose distribution already at the beginning of the optimization procedure, i.e. prior to the first optimization cycle. Instead, the user typically modifies the weights of the individual objective functions in the cost function. For example, if the user determines that a too high dose is delivered to an OAR, he/she may increase the weight of the individual objective function representing a maximum dose requirement for the relevant OAR.

By modifying the weights assigned to the objective functions, the user can only indirectly influence the dose distribution calculated in the next optimization cycle. Therefore, a dose distribution which is close to the desired dose distribution can usually only be achieved by iterative modifications in a trial and error approach. This is often very time-consuming and may also lead to unsatisfactory results.

EP 2 260 902 A1 discloses a radiation treatment planning system, in which a user can interactively specify a local dose variation and the systems revises the preliminary treatment plan such as to account for the inputted local dose variation. In order to revise the treatment plan, the system computes suitable adjustments of bixel weights such that the local dose changes as prescribed by the user. For this purpose, the weights of the bixels contributing to the dose of the relevant voxel may be changed in the same manner. As an alternative, only the bixel with the highest contribution to the local dose may be modified or those bixels may be modified, which have a relative contribution to the local dose that exceeds a predetermined threshold.

SUMMARY OF THE INVENTION

It is an object of the invention to allow for an easier and faster adaptation of a pre-optimized treatment plan.

In accordance with a first aspect, the invention suggests a system for planning a radiation therapy treatment of a target structure in a region of a patient body, wherein radiation delivered to the region comprises a plurality of radiation contributions which are individually controllable on the basis of a treatment plan. The system comprises a planning unit configured to (i) obtain a first treatment plan generated in accordance with values of parameters quantifying an amount of radiation provided by the radiation components and resulting in a first dose distribution in the region of the patient body, (ii) obtain an instruction to change a radiation dose delivered to at least one volume element of the region according to the first dose distribution, and (iii) directly calculate, for at least some of the radiation components, a change of the parameter value quantifying the amount of radiation provided by the radiation component on the basis of the contribution of the radiation component to the radiation dose delivered to the at least one volume element, (iv) calculate updated parameter values on the basis of the determined changes of the parameter values quantifying the amount of radiation provided by the radiation components, (v) determine a second treatment plan on the basis of the updated parameter values. The parameter values quantifying the changes of the amount of radiation provided by the radiation components are bound to an upper and/or lower threshold and the planning unit is configured to calculate the updated parameter values by iteratively adding the determined changes to the parameter values until a parameter value reaches the upper or lower threshold or until a dose distribution resulting from a treatment plan generated on the basis of the updated parameter values includes the changed dose of the at least one volume element The suggestion to directly calculate the changes of the parameter values quantifying the amount of radiation provided by the radiation components refers to a calculation procedure which avoids the indirect determination of these changes on the basis of the solution of an optimization problem. Such a direct calculation allows for modifying the treatment plan with less computational complexity so that an easier and faster modification of the treatment plan is achieved.

Moreover, the suggested system allows for directly specifying dose changes for specific volume elements. This particularly simplifies the modification of the treatment plan for the user compared with the conventional procedure in which the user has to modify an optimization problem in order to indirectly control modifications of the dose distribution resulting from the treatment plan.

The calculation of the changes of the parameter values quantifying the amount of radiation provided by the radiation components is preferably performed only with respect to the radiation components contributing to the radiation dose delivered to the at least one volume element. Moreover, the parameter values quantifying the amount of radiation provided by the relevant radiation components are preferably only adapted with respect to the radiation dose provided by these radiation components to the relevant at least one volume element in the calculation.

Thus, the calculation of the changes of the parameter values quantifying the amount of radiation provided by the radiation components is effectively carried out under the assumption that all dose changes only affect the volume elements for which a dose change is specified. Hereby, the dimensionality of the calculation and, thus, its computational complexity is further reduced so that the computation can be performed very fast.

In one embodiment, the contributions of the radiation components to the radiation dose delivered to the at least one volume element are adapted on the basis of a locality parameter and on the basis of the contribution itself in order to determine the change of the parameter value quantifying the amount of radiation provided by the radiation component. On the basis of the locality parameter, the contributions of the radiation components to the radiation dose absorbed by a certain volume elements may particularly be adapted such that lower contributions are further reduced relative to higher contributions in the process of determining the changed parameter values. As a result, the changes of the radiation components can be kept "local", i.e. they can essentially be restricted to a few radiation components. Hereby, it is possible to reduce the likelihood that the modifications of the treatment plan result in a violation of dose constraints which were already fulfilled by the first treatment plan. In particular, it is possible to prevent detrimental effects of the aforementioned limitations of the calculation to radiation components which provide radiation to the at least one volume element and to the radiation provided by these radiation components to the at least one volume element.

The suggested system may particularly be used for planning a brachytherapy treatment. In a related embodiment, each of the radiation components corresponds to radiation emitted by one of a plurality of radiation sources within the patient body during a dwell time and the parameter quantifying an amount of radiation provided by one radiation source corresponds to the associated dwell time.

Likewise, the suggested system is suitable for planning an external beam radiation therapy treatment. In a related embodiment, each of the radiation components corresponds to an element of a radiation beam generated by a radiation source external to the patient body and the parameter quantifying an amount of radiation provided by one element of a radiation beam corresponds to an associated fluence.

In a further embodiment, the planning unit is configured to determine the changes of the parameter values quantifying the amount of radiation provided by the radiation components on the basis of an influence matrix quantifying a contribution of the radiation components to individual volume elements of the region of the patient body. On the basis of the influence matrix, a linear approximation of the dose absorbed by the volume elements of the relevant region of the patient body is possible as a function of the (emitted) dose provided by the radiation components. In particular, each component of the influence matrix may quantify the amount of dose absorbed by a certain volume element per unit amount of radiation provided by a certain radiation component. The unit amount of radiation may be measured in accordance with a suitable quantity influencing the amount of radiation provided by the radiation component.

In case of a brachytherapy treatment, this quantity may particularly correspond to the dwell time of a radiation source. Thus, each component of the influence matrix may quantify an amount of dose absorbed by a certain voxel per unit time due to the emission from a certain radiation source at a certain position. In case of an external beam radiation therapy treatment, the quantity may particularly correspond to the fluence of a beam element. Thus, the influence matrix may quantify an amount of dose absorbed by a certain volume element due to an emission in a certain beam element per unit fluence.

In one embodiment, the planning unit is configured to determine the change of the parameter value quantifying the amount of radiation provided by the i-th radiation component in accordance with $$\Delta \tau_i = \sum_j [B \cdot (M_d \cdot B)^{-1}]_{ij} \Delta d_j,$$

where $\Delta \tau_i$ denotes the parameter value quantifying the amount of radiation provided by the i-th radiation component, $\Delta d_j$ denotes the amount of change of the radiation dose delivered to the volume element j, $[B \cdot (M \cdot B)^{-1}]_{ij}$ denotes the i,j-component of the matrix $B \cdot (M_d \cdot B)^{-1}$, $M_d$ denotes a matrix comprising the rows of the influence matrix which relate to the at least one volume element and B denotes a diagonal matrix generated on the basis of the influence matrix and a locality parameter α to achieve the adaptation of the contributions of the radiation components to the radiation dose delivered to the at least one volume element.

In case of a brachytherapy treatment, $\Delta \tau_i$ may correspond to a change of the dwell time of the i-th radiation source. In case of an external beam radiation therapy treatment, $\Delta \tau_i$ may correspond to a change of a fluence of the i-th element of a radiation beam in case of an external beam radiation therapy treatment.

In a further embodiment, each diagonal element $B_{ij}$ of the matrix B is calculated according to $$B_{jj} = \max_i P_{ij}^\alpha,$$

where $P_{ij}$ denotes the components of a matrix P which is obtained from the matrix $M_d$ by normalizing the components of each row using the maximum component of the respective row and the locality parameter α has values equal to or larger than zero. Preferably the value of the locality parameter α is larger than zero.

The instruction to change a radiation dose delivered to at least one volume element of the region according to the first dose distribution may be manually provided by a user of the planning unit, e.g. upon a review of the first dose distribution. In this respect, one embodiment includes that the planning unit is configured to identify in the first dose distribution at least one volume element absorbing the highest radiation dose and/or the lowest radiation dose and to determine changes of the parameters quantifying the amount of radiation provided by the radiation components to change the radiation dose delivered to said at least one volume element. The volume elements absorbing the highest radiation dose (so-called hottest spots) and the lowest radiation (so-called coldest spots) do most likely correspond to the volume elements for which the absorbed dose is to be modified. Thus, the automatic determination of the hottest and/or coldest spots by the planning unit assists the user in identifying the volume elements for which changes of the absorbed radiation dose may be necessary.

Further, the planning unit may be configured to receive a global dose constraint for the dose distribution corresponding to the second treatment plan. Such a global dose constraint may be specified by the user of the planning unit, e.g. on the basis of the dose volume histogram of the first dose distribution. With respect to the global dose constraint, the planning unit may be configured to identify at least one volume element such that a change of the radiation dose delivered to the at least one volume element in accordance with the first dose distribution results in a fulfillment of the global dose constraint and to generate an instruction to change the radiation dose delivered to the identified at least one volume element. Hereby, it is possible for the user to control the modification of the treatment plan on the basis of global dose constraints in addition or as an alternative to the modification on the basis of changes of the dose delivered to specific volume elements. The instructions relating to these changes are automatically generated by the system on the basis of the dose constraint in this embodiment.

In a related embodiment, a given fraction of a volume of the region of the patient absorbs a first radiation dose in accordance with the first dose distribution and the global dose constraint requires that the radiation dose delivered to the fraction is larger than a specified second dose value. In this case, the planning unit may be configured to identify at least one volume element absorbing a radiation between the first and second radiation dose and to generate an instruction to change the radiation delivered to said at least one volume element.

In a further embodiment, the planning unit is configured to provide a graphical user interface for rendering a graphical visualization of the first dose distribution to a user and to receive a user input for selecting the at least one volume element in the visualization.

In accordance with a further aspect, the invention suggests a method for planning a radiation therapy treatment of a target structure in a region of a patient body, wherein radiation delivered to the region comprises a plurality of radiation contributions which are individually controllable on the basis of a treatment plan. The method comprises the following steps: (i) obtaining a first treatment plan generated in accordance with values of parameters quantifying an amount of radiation provided by the radiation components and resulting in a first dose distribution in the region of the patient body, (ii) obtain an instruction to change a radiation dose delivered to at least one volume element of the region according to the first dose distribution, (iii) directly calculating, for at least some of the radiation components, a change of the parameter value quantifying the amount of radiation provided by the radiation component on the basis of the contribution of the radiation component to the radiation dose delivered to the at least one volume element, (iv) calculating updated parameter values on the basis of the determined changes of the parameter values quantifying the amount of radiation provided by the radiation components, and (v) determining a second treatment plan on the basis of the updated parameter values. the parameter values quantifying the changes of the amount of radiation provided by the radiation components are bound to an upper and/or lower threshold and the updated parameter values are calculated by iteratively adding the determined changes to the parameter values until a parameter value reaches the upper or lower threshold or until a dose distribution resulting from a treatment plan generated on the basis of the updated parameter values includes the changed dose of the at least one volume element In accordance with a further aspect, the invention suggest a computer program comprising program code for instructing a computer device to perform the method when the program code is executed in the computer device.

It shall be understood that the system of claim 1, the method of claim 12 and the computer program of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
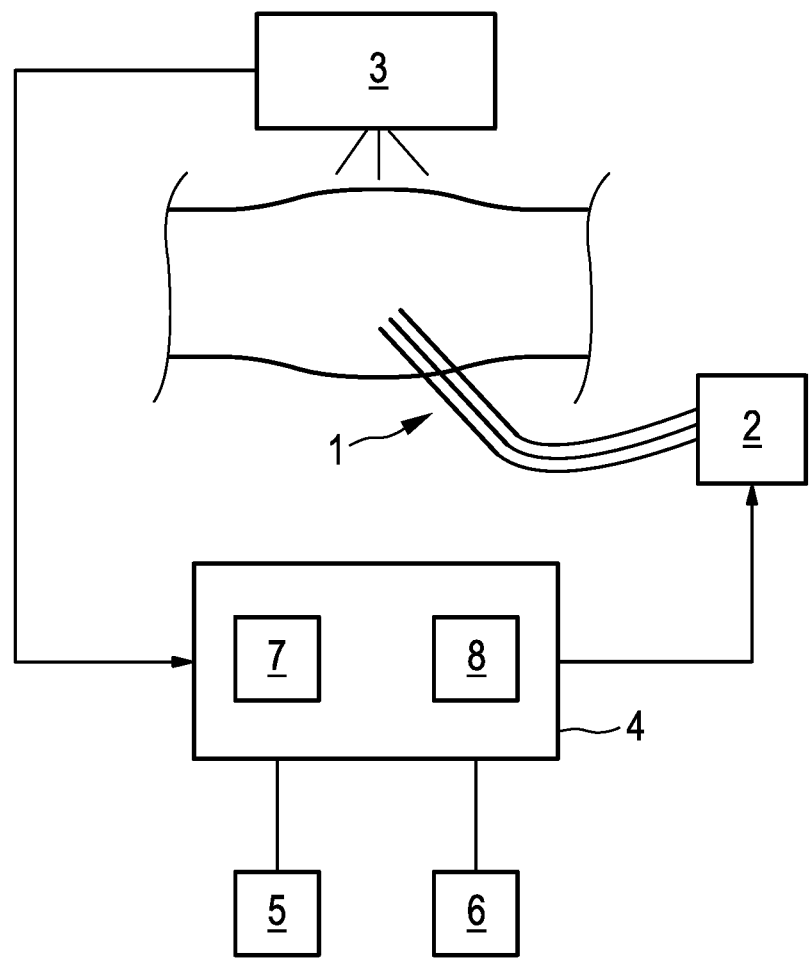
FIG. 1 schematically and exemplarily shows components of a brachytherapy system, FIG. 2 schematically and exemplarily shows components of an external beam radiation therapy system, FIG. 3 schematically and exemplarily steps of a procedure for modifying a treatment plan.
Figure 2:
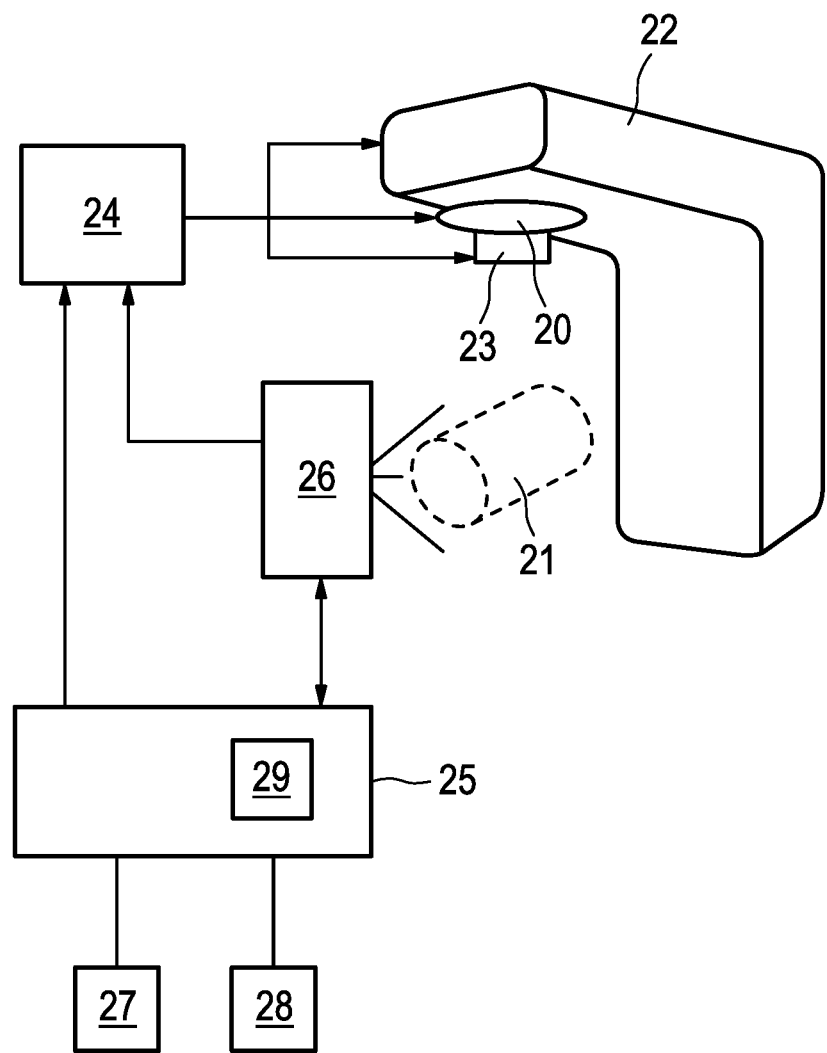

FIGS. 1 and 2 schematically and exemplarily illustrate embodiments of a system for delivering radiation therapy treatments to target structures within a human or animal patient body. The target structures may particularly be tumors within certain regions of the body. In one exemplary embodiment, which is schematically shown in FIG. 1, the system is configured as a temporal brachytherapy system, which may be configured to deliver a high-dose rate (HDR) brachytherapy treatment or another form of temporal brachytherapy treatment. In a further exemplary embodiment, which is schematically shown in FIG. 2, the system is configured as an external beam radiation therapy treatment system.

(Brachytherapy System)

In the brachytherapy system, the target structure is irradiated by means of one or more radiation source(s), which are temporarily placed in a treatment region in the vicinity of the target structure (where it is assumed in the following that plural radiation sources are used). The treatment may be delivered once or in plural fractions (i.e. radiation sources are placed in the treatment region several times).

The brachytherapy system comprises an applicator 1 for delivering the radiation sources to the treatment region. The radiation sources may particularly include radioactive particles emitting ionizing radioactive radiation for treating the target structure. The applicator 1 includes catheters for receiving the radiation sources. Via the catheters, the radiation sources can be delivered to the treatment region and hold at defined positions, which are also referred to as dwell positions, for defined time periods, which are also referred to as dwell times. In the embodiment illustrated in FIG. 1, the radiation sources are remotely delivered into the applicator 1 from an afterloader device 2. In further embodiments, the radiation sources can likewise be delivered manually into the applicator 1.

Further, the system comprises an imaging device 3 which is configured to acquire images of the treatment region within the patient body. Preferably, the imaging device 3 is configured to generate three-dimensional images of the treatment regions. For this purpose, the imaging device 3 may employ any suitable imaging modality known to a person skilled in the art. Exemplary imaging modalities employed by the imaging device 3 include computed tomography (CT), ultrasound imaging or magnetic resonance imaging (MRI). In principle, it is also possible that the imaging device 3 is configured to acquire two-dimensional images of the treatment region by means of x-ray imaging, ultrasound imaging or another imaging technique. On the basis of the images, the anatomical configuration of the treatment region can be inspected and the relative position of the radiation source(s) and the applicator 1 with respect to the target structure and OARs can be determined, when images are acquired while the applicator 1 is positioned in the treatment region.

The treatment is delivered in accordance with a treatment plan, which specifies the relevant treatment parameters particularly including the dwell times and which is generated in a planning unit 4, which will be described in more detail herein below. Before commencing an actual radiation treatment in the system, one or more appropriate dwell position(s) in the treatment region is/are determined in a positioning module 7 of the planning unit 4, and the applicator 1 is positioned in the treatment region such that the radiation source(s) are arranged at the determined dwell position(s) when being inserted into the applicator 1.

The dwell position(s) may be determined on the basis of the positions of the target structure and the OARs by applying a heuristic determination procedure. Known examples of such a procedure include the so called k-means clustering procedure and the so called centroidal Voronoi tessellation. The positions of the target structure and the OARs may be determined using an image of the treatment region acquired by means of the imaging device 3. In the image, the target structure and the OARs may be delineated to determine the contours of the target structure and the OARs, and the positions may be determined on the basis of the determined contours. The delineation of the target structure and the OARs may be made using a manual, semi-automatic or automatic procedure known to the person skilled in the art.

On the basis of the arrangement of the dwell position(s) relative to the target structure and the OARs, the treatment plan is determined in a plan module 8 of the planning unit 4 using an image of the relevant region of the patient body including the dwell positions, the target structure and the surrounding OARs. The treatment plan particularly defines the dwell time(s) during which the treatment region is irradiated by means of the radiation source(s). Upon having positioned the applicator 1 in the treatment region and upon having determined the treatment plan for the dwell position(s) of the radiation source(s), the radiation source(s) is/are delivered into the applicator 1 and hold in place within the applicator 1 in accordance with the treatment plan.

(External Beam Radiation Therapy System)

The external beam radiation therapy system comprises a radiation source 20, which can be operated to emit ionizing radiation into a treatment zone 21. In the treatment zone 21, the patient body is positioned on a suitable support, such as a patient table (not shown in the figures). The relative position and orientation of the radiation source 20 with respect to the relevant body region can be varied over a certain range of positions and orientations. For this purpose, the radiation source 20 may be mounted on rotatable gantry 22 so that the radiation source 201 can be rotated around the treatment zone 21 within a certain angular range, which may be 360° or less, in order to deliver radiation under different beam directions. In addition, the gantry 22 and/or the patient support may be movable in a direction parallel and/or perpendicular to the rotation axis of the gantry 22. Hereby, it is possible to set up a certain relative position between the patient and radiation isocenter such that the target structure is arranged within the radiation isocenter. Further, it may be possible to rotate the support around an axis perpendicular to the rotation axis of the gantry 22.

The radiation source 20 may include a linear particle accelerator or another radiation source for producing an ionizing radiation beam. One example of another radiation source is a radioactive source, such as a cobalt source. Further, the radiation source 20 may be provided with a collimator 23 for shaping the radiation beam. The collimator 23 may particularly allow for varying the radiation intensity across the radiation beam in a defined way. For this purpose, the collimator 23 may be configured as a multi-leaf collimator.

During delivery of the radiation therapy treatment, radiation is delivered to the target structure under varying beam directions and the intensity of the radiation emitted by the radiation source 20 may be varied. Moreover, the configuration of the collimator 23 may be changed based on the treatment plan so that the radiation beam is delivered with a time-varying shape. The related treatment parameters including the beam directions and intensities and the collimator configurations are defined in a treatment plan.

In one implementation, the radiation therapy treatment is delivered in accordance with successive segments, where each segment corresponds to one configuration of the treatment parameters defined in the treatment plan. In between two segments, the configuration is changed from the configuration of the first of the segments to the configuration of the second of the segments. During this period, the radiation beam may be turned off (this is usually also referred to as step-and-shoot approach). Likewise, it is possible to continuously change the configuration in accordance with the segments without interrupting the radiation beam. This approach is applied in so-called volume modulated arc therapy (VMAT), for example.

For controlling the components of the radiation therapy treatment system, including the radiation source 20, the collimator 23, the gantry 22 and the patient support, during the treatment, the treatment system includes a control unit 24. Preferably, the control unit 5 is implemented as a software program which comprises the control routines carried out by the control unit and which is executed in a computer device coupled to the further components of the radiation therapy treatment system.

The treatment plan may be generated in a planning unit 25 by means of a plan module 29 included therein prior to the treatment on the basis of an image of the relevant body region including the target structure and the surrounding OARs, which is also referred to as planning image herein. The planning image may be acquired using an imaging device 26 configured in accordance with a suitable imaging modality, which may be included in the system. If the system includes such an imaging device 26, it may also be possible to adapt the treatment plan during the course of the treatment on the basis of images acquired during the treatment in a way known to a person skilled in the art. As an alternative, the planning image may also be acquired using an imaging device external to the system.

(Generation of the Treatment Plan)

The generation of the treatment plan is generally performed in such a way that the amount of radiation provided by the individually controllable radiation components available in the respective radiation therapy system is optimized. The optimization is carried out in such a way that a sufficient radiation dose is delivered to the target structure and the radiation dose delivered to the OARs is kept below pre-defined thresholds. For this purpose, the planning unit 4, 25 of the radiation therapy system carries out an optimization procedure to determine values of parameters quantifying the amount of radiation provided by the individually controllable radiation components and generates the treatment plan on the basis of these parameter values.

In the brachytherapy system, the individually controllable radiation components correspond to the radiation emitted by the radiation sources placed in the patient body. The parameters to be optimized in the planning of a brachytherapy system may particularly correspond to the dwell times of the radiation sources which determine the amount of radiation emitted by the radiation sources during the treatment. In the external beam radiation therapy system, the individually controllable radiation components correspond to the available beamlets, i.e. the beamlets which can be generated in the system particularly in accordance with the possible beam directions relative to the target structure and the possible collimator configurations, where one beamlet corresponds to a portion of a radiation beam when the beam is divided using a preferably regular grid. The parameters to be optimized may particularly correspond to the fluences of the beamlets and on the basis of the optimized fluences the planning unit 4 may determine the machine parameters to be specified in the treatment plan. Likewise, it is possible that the machine parameters are directly optimized.

The planning units 4, 25 for generating the treatment plans in both systems are configured in a similar way. In particular, each planning unit 4, 25 may be configured as a computer device, such as, for example a personal computer, comprising a processing unit which executes a treatment planning software for generating treatment plans for controlling the execution of the radiation therapy treatment. Each planning unit 4, 25 comprises a suitable interface for receiving a planning image acquired as explained above. Further, each planning unit 4, 25 comprises or is coupled to a user interface for interacting with a user (which may e.g. be a physician). The user interface may particularly comprise a display unit 5, 27 and an input device 6, 28. The input device 6, 28 may particularly allow for navigating within a graphical user interface provided on the display unit 5, 27. For this purpose, the input device 6, 28 may particularly comprise a pointing device, such as, for example, a computer mouse, a track pad or a trackball. Likewise, the display unit 5, 27 may comprise a touch-sensitive monitor which also serves as input device 6, 28.

In each planning unit 4, 26, the treatment plan is generated in the corresponding plan module 8, 29 on the basis of a clinical prescription for the patient, which may particularly specify treatment goals with respect to the target structure. These treatment goals may include the delivery of a certain minimum radiation dose to the target structure during the treatment. In addition, treatment goals with respect to the OARs may be specified. These treatment goals may include the delivery of maximum radiation doses to be delivered to the OARs. Moreover, the treatment plan is generated on the positions of the target structure and the OARs determined in accordance with the planning image. For this purpose, the delineations of the target structure and the OARs are determined in the planning image using a suitable delineation procedure, which may be a manual, semi-automatic or automatic delineation procedure.

On the basis of the treatment goals, a set of soft and/or hard constraints is determined and a pre-optimized treatment plan is generated which at least approximately fulfills the constraints. For this purpose, an optimization problem is formulated on the basis of the constraints, and this optimization problem is at least approximately solved.

Soft constraints correspond to requirements that the dose distribution should fulfill. The possible soft constraints particularly comprise the delivery of a maximum and minimum radiation dose to specific locations or regions within the treatment region. Minimum dose requirements usually relate to the target structure. So a minimum radiation dose to be delivered to one or more locations or regions of the target structure may particularly be specified. Maximum dose requirements usually relate to the OARs. In this regard, a maximum radiation dose to be delivered to one or more locations or regions of the OARs may particularly be specified. In addition, further soft constraints may be defined, such as, for example, the delivery of a uniform dose distribution to a certain region of the treatment volume (which will usually be a region of the target structure).

Hard constraints generally correspond to the same requirements as the soft constraints. However, while requirements implemented as soft constraints do not have to be exactly fulfilled, the dose distribution must no violate requirements implemented as hard constraints.

In order to automatically generate the pre-optimized treatment plan on the basis of the soft and hard constraints specified for a particularly patient, the plan module 8, 29 may minimize a cost function F using a suitable optimization algorithm. The cost function F may comprise a collection of individual objective functions $F^k$, where each individual objective function $F^k$ represents one soft constraint. In one embodiment, the cost function F may particularly correspond to a weighted sum of the objective functions $F^k$, i.e.

$$F(\tau) = \sum_{k=1}^{N} w^k F^k,$$

where $\tau$ denotes the set of treatment parameters to be determined and the parameter $w^k$ denotes the weight of the objective function $F^k$. Due to the weighting, soft constraints having a higher weight are satisfied more likely than soft constraints having a lower weight, in case such soft constraints are in conflict with each other. Hence, the weights are selected in accordance with the importance of the soft constraints with respect to the success of the treatment.

The hard constraints correspond to side conditions which have to be fulfilled by the solution of the optimization problem. In particular, a hard constraint may be represented by a function $C(\tau)$ so that the plan module 8, 29 may minimize the aforementioned function $F(\tau)$ and may at the same time ensure that $$C(\tau) \geq 0 \text{ or } C(\tau) = 0$$

is fulfilled.

The objective functions and the individual hard constraints usually depend on a variable radiation dose resulting from the treatment plan and on related dose goal for certain volume elements of the relevant region of the patient body, where the volume elements may correspond to the voxels of the planning volume as included planning images. In particular, these voxels may result from a division of the planning volume in accordance with a regular grid.

As an example, the objective function representing a maximum/minimum radiation dose for a certain volume V may be given by $$F^k = \sum_{i \in V} f(d_i, d^k) \cdot \left[\frac{d_i - d^k}{d^k}\right]^2 \cdot \Delta v_i,$$

where $f(d_i, d^k) = H(d_i - d^k)$ in case a maximum dose is specified and $f(d_i, d^k) = H(d^k - d_i)$ in case a minimum dose is specified. $\Delta v_i$ denotes the volume of the voxel i, $d_i = d_i(\tau)$ is the radiation dose delivered to the voxel i when the radiation parameters $\tau$ are used, $d^k$ is the maximum/minimum radiation dose to be delivered to the volume V, and H is the Heaviside step function defined by $$H(x) = \begin{cases} 0, & x < 0 \\ 1, & x \geq 0 \end{cases}.$$

For instance, the corresponding function C for a hard constraint corresponding to a maximum dose requirement may be $C = d^k - d_i$ and the function C for a hard constraint corresponding to a minimum dose requirement may be $C = d_i - d^k$. In order to (approximately) solve the optimization problem such that the hard constraints are fulfilled, the known method of Lagrangian multipliers can be applied, for example.

The variable radiation doses (i.e. the doses $d_i$ in the aforementioned examples) are functions of the treatment parameters to be determined. In case of the brachytherapy system, the radiation doses are functions of the dwell times for the dwell positions. In case of the external beam radiation therapy system, the radiation doses are functions of the fluences of the beamlets of the radiation beams generated in the different segments of the treatment.

In particular, the radiation dose absorbed by the voxel i of the relevant region of the patient body may be linearly approximated on the basis of an influence matrix. In case of the brachytherapy system, the approximation may be calculated in accordance with $$d_i = \sum_j M^B_{ij} \cdot t_j$$

where $M^B_{ij}$ denotes the i,j-component of the influence matrix $M^B$ for brachytherapy and $t_j$ denotes the dwell time of the dwell position j. Each component $M^B_{ij}$ of the influence matrix quantifies the amount of dose absorbed by the voxel i per unit time due to emission from the radiation source at dwell position j. The influence matrix may be calculated on the basis of the dwell positions (determined as explained above), the anatomical configuration of the relevant region of the patient body and the known radiation intensity emitted by the radiation sources.

In case of the external radiation therapy system, the radiation dose absorbed by the voxel i may be approximated in accordance with $$d_i = \sum_j M^E_{ij} \cdot \varphi_j,$$

where $M^E_{ij}$ denotes the i,j-component of the influence matrix $M^E$ for external beam radiation therapy and $\varphi_j$ denotes the fluence of the beamlet j. Each component $M^E_{ij}$ of the influence matrix quantifies the amount of dose absorbed by the voxel i per unit fluence from the beamlet j. The influence matrix $M^E$ may be determined on the basis of the anatomical configuration of the relevant region of the patient body for the relevant beam directions of the radiation beam and the corresponding beamlets.

These approximations may be used in generating the objective function $F^k$ and the constraints for determining the treatment plan. Likewise the other approximations, such as, for example, approximations on the basis of non-linear models may be used for this purpose. In case of the brachytherapy system, the generated objective function $F^k$ and the constraints are functions of the dwell times $t_i$ as optimization parameters which are to be determined. In case of the external beam radiation therapy system, the generated objective function $F^k$ and the constraints may be functions of the fluences $\varphi_j$ and these fluences may correspond to the optimization parameters which are to be determined. From the optimized fluences, the planning unit 4 may determine the machine parameters a model of the radiation source 1 and the collimator 4 and these machine parameters may be included in the treatment plan. This approach is also referred to as fluence map optimization (FMO).

As an alternative approach for determining the treatment plan for the external beam radiation therapy system, the optimization parameters corresponds to the machine parameters of the system. This approach is also referred to as direct machine parameter optimization (DMPO). In this variant, a model of the radiation source 20 and the collimator 23, which links the fluences with the machine parameters, is incorporated into the optimization problem so that the machine parameters are directly optimized. Using this model, the dose distribution is included into the objective function $F^k$ as a function of the machine parameters in DMPO rather than as a function of the fluences.

In order to solve the optimization problem and generate the pre-optimized treatment plan, the plan module 8, 29 may carry out an automatic numerical calculation. Optionally, it is also possible to carry out a user-guided iterative optimization procedure comprising several steps. In each step, the plan module 8, 29 automatically calculates a preliminary treatment plan by approximating a solution of the optimization problem. Then, the plan module 8, 29 determines the dose distribution corresponding to this treatment plan and visualizes the dose distribution to the user of the planning unit 4, 26. The user reviews the dose distribution to decide whether he/she is largely satisfied with the dose distribution (where the treatment goals do not have to be completely fulfilled as will be described herein below). If this is the case in one step, the treatment plan calculated in this step is used as the pre-optimized treatment plan. If the user is not satisfied, the optimization problem is modified in accordance with changes specified by the user as a result of his/her review. Then, the plan module 8 calculates a new preliminary treatment plan in the next step.

Upon this step, the plan module 8, 29 carries out a conventional treatment planning procedure. However, other than in conventional treatment planning, only a pre-optimized treatment plan is generated in the aforementioned steps, which is further optimized in subsequent steps described herein below to generate the final treatment plan. In contrast to the final treatment plan, the pre-optimized treatment plan may not completely fulfill the treatment goals and may particularly result in volumes, which still receive a lower radiation dose than desired (cold spots) or a higher radiation dose than desired (hot spots). Such an imperfect pre-optimized treatment plan can be calculated relatively quickly in a fully automatic numerical calculation or in few steps of the aforementioned user-guided optimization procedure. In particular, if a user-guided optimization procedure is carried, the operator may already stop the procedure if the treatment goals are roughly fulfilled, which is typically the case after few steps.

Upon having generated the pre-optimized treatment plan, the plan module 8, 29 obtains instructions to change the dose absorbed by one or more voxels. These instructions may relate to one or more voxels for which the dose constraints are violated in the dose distribution resulting from the pre-optimized treatment plan. Therefore, the voxels for which dose changes are specified are also referred to as violating voxels herein below. The instructions specify the relevant voxels the dose of which is to be changed and the amount of change of the dose values of the voxels or the target dose values of the voxels to be achieved.

On the basis of these instructions, the plan module 8, 29 determines for each of the separately controllable radiation components of the radiation delivered to the relevant region of the patient body a change of a parameter value quantifying the amount of radiation provided by the radiation component. The change of the parameter value is determined on the basis of the contribution of the respective radiation component to the radiation dose absorbed by the violating voxels. For this purpose, the changes of the parameter values may particularly be determined on the basis of the influence matrix M, which quantifies the influence of the radiation components to the voxels of the relevant region of the patient body as explained above.

As already explained above, the separately controllable radiation components in the brachytherapy system correspond to the radiation emitted by the different radiation sources placed in the patient body and the parameter quantifying the amount of radiation provided by these radiation components may correspond to the dwell times of the radiation sources. In the external beam radiation therapy system, the separately controllable radiation components correspond to the beamlets and the parameter quantifying the amount of radiation provided by these radiation components may correspond to the fluences of the beamlets.

The calculation of the changes of the parameter values quantifying the amount of radiation provided by the radiation components is preferably performed only on the basis of the radiation components contributing to the radiation dose delivered to the violating voxels and the parameter values quantifying the amount of radiation provided by the relevant radiation components are only adapted with respect to radiation dose provided by these radiation components to the violating voxels. This approach allows for a fast computation. However, it involves the assumption that only the doses absorbed by the relevant voxels change as a result of the adaption of the treatment plan. This assumption corresponds to an approximation which usually not reflects the actual dose changes resulting from the adaption of the amount of radiation provided by one or more radiation components.

In addition, the changes of the parameter values may therefore be calculated on the basis of a locality parameter. Using the locality parameter, the contributions of the radiation components to the radiation dose absorbed by a certain voxels may additionally be modified such that lower contributions are further reduced relative to higher contributions in the process of determining the changed parameter values. Hereby, it is achieved that greater changes of the amount of radiation provided by the radiation components only occur for the radiation components having the greatest contribution to the radiation dose absorbed by the voxels for which the dose value is to be changed. Thus, the changes of the radiation components are kept "local". Hereby, small deficiencies of the pre-optimized treatment plan can be removed without impairing the overall treatment plan (which already fulfilled the treatment goals to a large extent). In particular, detrimental effects of the aforementioned approximation can be prevented or at least reduced.

As a consequence of the utilization of the locality parameter in the brachytherapy system (and depending on the value of the locality parameter), the radiation amount provided by the radiation source placed closer to the violating voxels to greater extent than the amount of radiation provided by radiation sources having a greater distance from these voxels. In the external beam radiation therapy system, the amount of radiation of beamlets passing the violating voxels in a shorter distance is modified to a larger extent due to the utilization of the locality parameter (with an appropriate value).

In one embodiment, the changes of the parameter values quantifying the amount of radiation provided by the radiation sources are calculated according to $$\Delta\tau = B \cdot (M_d \cdot B)^{-1} \Delta d,$$

or, for the individual components of $\Delta\tau$, according to $$\Delta\tau_i = \sum_j [B \cdot (M_d \cdot B)^{-1}]_{ij} \Delta d_j$$

Here, $\Delta\tau$ denotes a vector having components $\Delta\tau_i$ which correspond to the parameters quantifying the amount of radiation provided by the radiation components i contributing to the dose absorbed by the violating voxels (i.e. the voxels for which the absorbed dose is to be modified) and $\Delta d$ denotes a vector having components $\Delta d_j$ specifying the desired changes of the radiation doses absorbed by the violating voxels j of the relevant region of the patient body. $M_d$ denotes a matrix comprising the rows of the influence matrix M for the respective treatment modality, which relate to the violating voxels. B denotes a square diagonal matrix having diagonal element $B_{ii}$ which are non-zero (the other components $B_{ij}$, i≠j, of the matrix B are zero).

The matrix B is preferably generated on the basis the influence matrix M of the respective treatment modality and a positive locality parameter $\alpha$ to achieve the aforementioned modification of the contributions of the radiation components to the dose absorbed by the violating as quantified by the matrix $M_d$. For this purpose a heuristic procedure may applied. In one related implementation, the elements $B_{jj}$ may be calculated according to $$B_{jj} = \max_i P_{ij}^\alpha,$$

where $\alpha$ is the locality parameter having values equal to or larger than zero and $P_{ij}$ denotes the components of a matrix P which is obtained from the matrix $M_d$ by normalizing the components of each row using the maximum component of the respective row. The maximum in the aforementioned equation is to be calculated within the column j over the rows i of P. Upon the aforementioned normalization the component $P_{xy}$ of the matrix P which relates to the radiation component y having the largest contribution to the dose absorbed by a violating voxel x has the value $P_{xy}=1$.

The locality parameter $\alpha$ in the aforementioned equation determines the "locality" of the changes of the amount of radiation provided by the radiation components in the aforementioned sense. For $\alpha=0$, all radiation components are treated as being equally important to achieve the desired modification of the dose distribution. In this case, the matrix B corresponds to the identity matrix. However, for $\alpha>0$ the amount of radiation provided by radiation components having a lower contribution to the dose absorbed by the violating voxels is modified to a smaller extent.

The value of the locality parameter $\alpha$ may be pre-configured in the plan module 8, 29 or may be specified by the operator of the planning unit 4, 25. Values for achieving good results may be between 1 and 5.

In accordance with the aforementioned principles, the plan module 8 of the brachytherapy system may particularly determine changes $\Delta t_i$ of the dwelling times $t_i$ by calculating the vector $$\Delta t = B^B \cdot (M_d^B \cdot B^B)^{-1} \Delta d$$

where the components of the vector $\Delta t$ correspond to the dwelling times $\Delta t_i$ and where $B^B$ corresponds to the matrix obtained from the influence matrix $M^B$ as explained above.

Similarly, the plan module 29 of the external beam radiation therapy system may determine changes $\Delta\varphi_i$ of the fluences of the beamlets i considered in the pre-optimized treatment plan by calculating $$\Delta\varphi = B^E \cdot (M_d^E \cdot B^E)^{-1} \Delta d$$

where the components of the vector $\Delta\varphi$ correspond to the fluences $\Delta\varphi_i$ and where $B^E$ corresponds to the matrix obtained from the influence matrix $M^E$ as explained above.

In a further embodiment, the changes of the parameter values quantifying the amount of radiation provided by radiation sources are calculated for each radiation component j on the basis of a weighted sum of the desired dose changes for the violating voxels, where the weights are determined based on influences of the radiation provided by the respective radiation component j on the dose absorbed by the violating voxels. These influences may again be determined using the influence matrix M. In addition, the changes are preferably calculated again on the basis of a locality parameter $\alpha$ having the above-described effect. In a specific implementation of this embodiment, the changes are calculated according to $$\Delta\tau_j = \frac{1}{N_d} \sum_{i=1}^{N_d} \Delta d_i \frac{M_{ij}^\alpha}{\sum_{k=1}^{N_t} M_{ik}^{\alpha+1}},$$

where $N_d$ is the number of violating voxels and $N_t$ is the number of radiation components. This approach likewise ensures the "locality" of the modifications of the amount of radiation provided by the radiation components on the basis of the locality parameter $\alpha$. Compared with the aforementioned embodiment, it is an advantage of this embodiment that no matrix inversion has to be carried out, which may not be possible in all cases.

On the basis of the changes of the parameter values quantifying the amount of radiation provided by the radiation components, the plan module 8, 29 determines new values of these parameters by adding the changes to the values of the parameters underlying the pre-optimized treatment plan. Using the new values, the plan module 8, 29 then determines an updated treatment plan, which may be further amended in the aforementioned way or which may be used for controlling the treatment if the operator of the planning unit 4 is satisfied with the dose distribution resulting from the updated treatment plan.

In practice, the parameters quantifying the amount of radiation provided by the radiation components, such as the dwell times and the beamlet fluences in the brachytherapy system and the external radiation therapy system, may be bound by upper and/or lower thresholds. Therefore, the updated parameters determined on the basis of the calculated changes may have invalid values which are higher than the upper threshold or lower than the lower threshold.

In order to determine updated parameters within the prescribed boundaries, the plan module 8, 29 may iteratively add the determined changes to the parameter values. In each step of the iterative procedure, the plan module 8, 29 may add the determined changes to the parameter values calculated in the previous step or, in the first step, to the parameter values underlying the pre-optimized treatment plan. An exception only applies for the parameter values which exceed the upper threshold or fall below the lower threshold upon the addition of the related changes. These parameter values may be set to the respective threshold values and may be held at these values for the rest of the procedure. Then, the plan module 8, 29 assesses whether the treatment plan determined on the basis of the resulting parameter values leads to a dose distribution comprising the desired changes of the dose values absorbed by certain voxels. If this is not the case, the next iteration step is carried out. Otherwise, the procedure terminates and the parameter values of the respective iteration step are further used for determining an updated treatment plan. Likewise, the procedure may terminate upon the completion of a number of iteration steps, which may be specified by the operator the planning unit 4, 25. In this case, the desired changes of the dose distribution cannot be achieved and, thus, no updated treatment plan is generated.

The aforementioned procedure for adapting the pre-optimized treatment plan may be controlled by an operator of the planning unit 4, 25 using a graphical user interface provided by the planning unit. In this graphical user interface, the planning unit 4, 25 may provide a visualization of the dose distribution resulting from the pre-optimized treatment plan. Optionally, this visualization may be overlaid over the relevant planning image in order to ease orientation of the operator.

In the graphical user interface, the operator may indicate voxels for which the absorbed radiation dose is to be changed in relation to the value corresponding to the visualized dose distribution. For this purpose, the operator may select the relevant voxels by moving a cursor to these voxels and performing an input operation at the input device, for example. Moreover, the operator may specify the changes of the dose values for the selected voxels by means of a corresponding user input. On the basis of these instructions indicating particular voxels and of the dose values to be delivered to these voxels, the plan module 8, 29 than calculates updated parameter values quantifying the amount of radiation provided by the radiation components and determines an updated treatment plan as explained above.

Moreover, the planning unit 4 may be configured to automatically detect a number of voxels to which the highest radiation dose is delivered in accordance with the dose distribution resulting from pre-optimized treatment plan and a number of voxels to which the lowest radiation dose is delivered in accordance with this dose distribution. These voxels correspond to the "hottest spots" and "coldest spots" of the dose distribution and it is most likely that the operator wishes to modify the dose values for these voxels. Therefore, these voxels may be highlighted in the graphical user interface and/or specified in a list so that the user can easily identify these voxels and select them for adapting their dose values as explained above.

In the embodiments described above, the plan module 8, 29 modifies the treatment plan such that local hot or cold spots of the resulting dose distribution are removed. In addition, the plan module may be configured to modify the treatment plan such that the resulting dose distribution fulfills modified global dose constraints.

Such global dose constraints may particularly relate to the so-called cumulative dose volume histogram (DVH), which illustrates which fractions of a certain volume, such as the target structure, absorbs at least a certain radiation dose. More specifically, such a DVH may be plotted with radiation doses on the horizontal axis and fractions of the relevant volume on the vertical axis, where value provided in the diagram specifies the fraction of the volume which absorbs at least the associated dose value.

Dose constraints relating to the DVH may include D and V constraints. A D constraint may be written as D [v %]>[d] Gy and requires that the radiation dose absorbed by v % of a certain volume, such as the volume of the target structure, is greater than d Gy. For instance, the dose constraint "D95>19 Gy" for the target structure requires that 95% of the volume of the target structure absorb a dose greater than 19 Gy. A V constraint may be written as V [x Gy]>[y]% and requires that the fraction of a certain volume that absorbs a dose of at least x Gy is greater than y % of the volume.

In order to assess the dose distribution resulting from the pre-optimized treatment plan, the operator of the planning unit 4, 25 may review the corresponding DVH and may modify the dose distribution by manipulating the DVH on the basis of D and V constraints. These constraints may be newly specified by the operator or the operator may modify corresponding constraints which were already used for determining the pre-optimized treatment plan.

When a new D constraint is specified by the operator for a certain fraction of the volume, the plan module 8, 29 determines a set of voxels violating this constraint. In particular, the plan module 8, 29 determines the voxels which absorb a dose between the dose value included in the DVH of the dose distribution resulting from pre-optimized treatment plan for the relevant fraction and the dose value specified by the operator in the D constraint. Thus, when v % of a volume absorb a dose of $d_0$ in accordance with the dose distribution resulting from the pre-optimized treatment plan and when the operator specifies that v % of this volume shall absorb a dose of $d_{new}$, the plan module determines the voxels of the volume absorbing a dose between $d_0$ and $d_{new}$.

As the skilled person will appreciate, the new D constraint will be fulfilled when the doses absorbed by the voxels determined in this manner is modified to correspond to the new dose value specified by the operator. This is due to the fact that the voxels absorbing at least a dose $d_0$ correspond to v % of the relevant volume (in accordance with the DVH). Thus, when all these voxels absorb a dose of at least $d_{new}$, the new D constraint will be fulfilled. This can be achieved by changing the dose absorbed by the relevant voxels currently absorbing a dose less then $d_{new}$ to this value. These voxels correspond to the voxels absorbing a dose between $d_0$ and $d_{new}$ in accordance with the current dose distribution.

Therefore, the plan module 8, 29 automatically specifies the dose value $d_{new}$ input by the user for the new dose constraint as the target dose value for the voxels identified in the aforementioned way and determines a new treatment plan using these target values as explained above.

When the operator specifies a new V constraint, the plan module 8, 29 may convert this V constraint to a corresponding D constraint. Thus, if the operator specifies a new volume constraint "Vx>y %", the plan module converts this volume constraint to the dose constraint "Dy>x Gy". Since the DVH curves are monotonically decreasing, this dose constraint ensures that the new volume constraint is also fulfilled. Upon the conversion, the plan module 8, 29 may determine a new treatment plan as described above in connection with the D constraint.

Moreover, if the treatment plan is modified as described so far, the modified treatment plan may result in a dose distribution in which the absorbed dose is changed for voxels which have not been identified as violating voxels in the modification procedure. Such changes may result in a violation of dose constraints which were fulfilled in the dose distribution resulting from the pre-optimized treatment plan. In view of this, one embodiment provides that the operator may specify "locked" dose constraints, which (still) have to be fulfilled by the dose distribution resulting from the modified treatment plan.

Upon performing a first modification of the pre-optimized treatment plan as explained above, the plan module 8, 29 may check whether the dose distribution resulting from the modified treatment plan fulfills the locked dose constraints. If this is not the case, the plan module 8, 29 may determine the voxels violating these dose constraints and may automatically specify modified dose values for these voxels in accordance with the violated dose constraints and may iteratively apply the above-described procedure to modify the treatment plan on the basis of the modified dose values until the locked dose constraints are fulfilled (or a predefined number of iterations has been reached). In each step of the iteration procedure, the plan module determines the voxels (still) violating the relevant dose constraints in the dose distribution resulting from the treatment plan determined in the preceding iteration step and specifies modified dose values for these voxels according to the dose constraints for the determination of a modified treatment plan in the current step.

Figure 3:
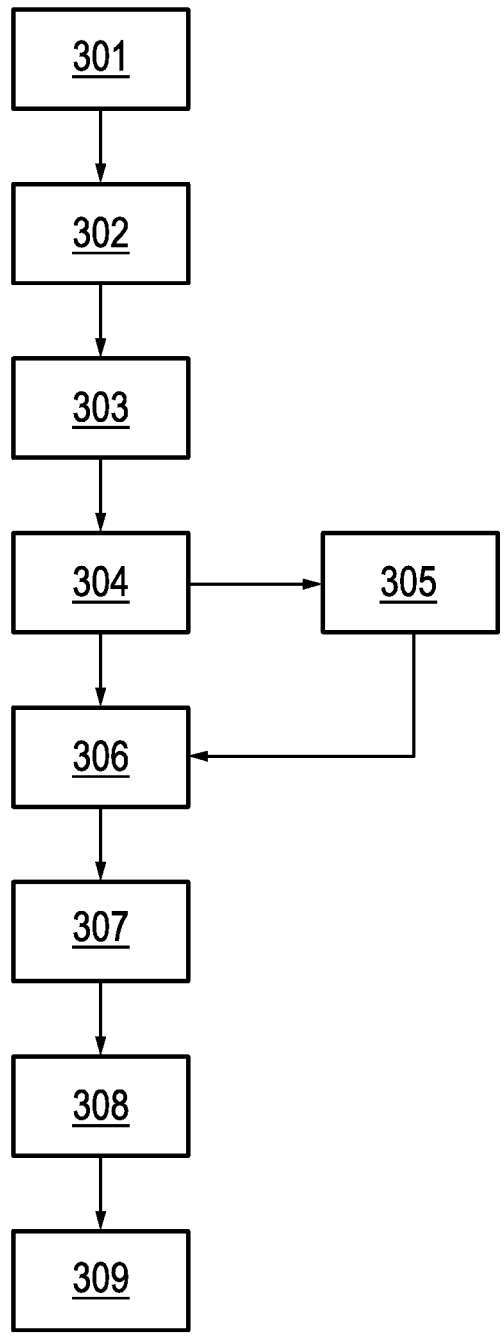

FIG. 3 illustrates exemplary steps of a procedure for modifying a pre-optimized treatment plan in the brachytherapy system or the external radiation therapy system described above: In step 301, the plan module 8, 29 of the planning unit 4, 25 obtains the pre-optimized treatment plan. Then, the plan module 8, 29 determines the dose distribution resulting from the pre-optimized treatment plan and visualizes this dose distribution to the operator by means of the display unit 5, 27 in step 302. Optionally the plan module 8, 29 may also detect the hottest and coldest spots in the dose distribution and may present these spots to the operator, e.g. by highlighting the corresponding voxels in the visualization of the dose distribution (step 303). In addition, the plan module 8, 29 may determine the DVH of the dose distribution and present it to the operator.

In step 304, the plan module 8, 29 receives user inputs specifying changes of doses delivered to one or more voxels. In addition, the plan module may receive one or more global dose constraints specified by the user particularly including D and/or V constraints as described above. For these global dose constraints, the plan module 8, 29 determines the violating voxels and specifies changed values of the radiation dose delivered to these voxels as explained above (step 305). Thereupon, instructions to change the radiation doses delivered to one or a number of voxels are present in the plan module 8, 29. These instruction directly correspond to the user input in step 304 for the voxels for which the user directly specified dose values and they are automatically generated by the plan module for the voxels identified in step 305 on the basis of the global dose constraints.

In step 306, the plan module 8, 29 determines changes of the parameter values quantifying the amount of radiation provided by the relevant radiation components of the respective system in a way explained above. On the basis of these changes, the plan module 8, 29 calculates updated values of the relevant parameters (step 307). Using these updated values, the plan module 8, 29 determines a modified treatment plan in step 308.

In step 309 the plan module 8, 29 may determine the dose distribution resulting from the modified treatment plan and may visualize this dose distribution to the operator for inspection. If the operator is satisfied with the dose distribution, the modified treatment plan may be used for delivering the treatment. If the operator is not satisfied, further modification of the dose distribution and the treatment plan may be made similar to the first modifications.

In such a way an easy and quick optimization of a pre-optimized treatment plan for a brachytherapy treatment or an external beam radiation therapy treatment can be carried out. In a similar way, a treatment plan can be generated and optimized in other ablation therapy modalities, such as HIFU, radio frequency (RF) and microwave treatments and laser ablation. In HIFU, the relevant dose may correspond to a thermal dose and the radiation may correspond to ultrasound waves, which are also encompassed by the term radiation as used herein.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for planning a radiation therapy treatment of a target structure in a region of a patient body, wherein radiation delivered to the region comprises a plurality of radiation contributions which are individually controllable on the basis of a treatment plan and wherein the system comprises a planning unit configured to:

obtain a first treatment plan generated in accordance with values of parameters quantifying an amount of radiation provided by the radiation components and resulting in a first dose distribution in the region of the patient body, obtain an instruction to change a radiation dose delivered to at least one volume element of the region according to the first dose distribution, and directly calculate, for at least some of the radiation components, a change of the parameter value quantifying the amount of radiation provided by the radiation component on the basis of the instruction and on the basis of the contribution of the radiation component to the radiation dose delivered to the at least one volume element, calculate updated parameter values on the basis of the determined changes of the parameter values quantifying the amount of radiation provided by the radiation components, determine a second treatment plan on the basis of the updated parameter values, wherein the parameter values quantifying the changes of the amount of radiation provided by the radiation components are bound to an upper and/or lower threshold and wherein the planning unit is configured to calculate the updated parameter values by iteratively adding the determined changes to the parameter values until a parameter value reaches the upper or lower threshold or until a dose distribution resulting from a treatment plan generated on the basis of the updated parameter values includes the changed dose of the at least one volume element.

2. The system as defined in claim 1, wherein the contributions of the radiation components to the radiation dose delivered to the at least one volume element are adapted on the basis of a locality parameter and on the basis of the contribution itself in order to determine the change of the parameter value quantifying the amount of radiation provided by the radiation component.

3. The system as defined in claim 1, wherein each of the radiation components corresponds to radiation emitted by one of a plurality of radiation sources within the patient body during a dwell time and wherein the parameter quantifying an amount of radiation provided by one radiation source corresponds to the associated dwell time.

4. The system as defined in claim 1, wherein each of the radiation components corresponds to an element of a radiation beam generated by a radiation source external to the patient body and wherein the parameter quantifying an amount of radiation provided by one element of a radiation beam corresponds to an associated fluence.

5. The system as defined in claim 1, wherein the planning unit is configured to determine the changes of the parameter values quantifying the amount of radiation provided by the radiation components on the basis of an influence matrix quantifying a contribution of the radiation components to individual volume elements of the region of the patient body.

6. The system as defined in claim 2, wherein the planning unit is configured to determine the change of the parameter value quantifying the amount of radiation provided by the i-th radiation component in accordance with $$\Delta \tau_i = \sum_j [B \cdot (M_d \cdot B)^{-1}]_{ij} \Delta d_j,$$

where $\Delta \tau_i$ denotes the parameter value quantifying the amount of radiation provided by the i-th radiation component, $\Delta d_j$ denotes the amount of change of the radiation dose delivered to the volume element j, $[B \cdot (M \cdot B)^{-1}]_{ij}$ denotes the i,j-component of the matrix $B \cdot (M_d \cdot B)^{-1}$, $M_d$ denotes a matrix comprising the rows of the influence matrix which relate to at least one volume element and B denotes a diagonal matrix generated on the basis of the influence matrix and a locality parameter $\alpha$ to achieve the adaptation of the contributions of the radiation components to the radiation dose delivered to the at least one volume element.

7. The system as defined in claim 6, wherein $\Delta \tau_i$ denotes a change of the dwell time of the i-th radiation source or a change of a fluence of the i-th element of a radiation beam.

8. The system as defined in claim 6, wherein each diagonal element $B_{jj}$ of the matrix B is calculated according to $$B_{jj} = \max_i \ P_{ij}^\alpha,$$

where $P_{ij}$ denotes the components of a matrix P which is obtained from the matrix $M_d$ by normalizing the components of each row using the maximum component of the respective row and the locality parameter $\alpha$ has values equal to or larger than zero.

9. The system as defined in claim 1, wherein the planning unit is configured to identify in the first dose distribution at least one volume element absorbing the highest radiation dose and/or the lowest radiation dose and to determine changes of the parameters quantifying the amount of radiation provided by the radiation components to change the radiation dose delivered to said at least one volume element.

10. The system as defined in claim 1, wherein the planning unit is configured to receive a global dose constraint for the dose distribution corresponding to the second treatment plan, to identify at least one volume element such that a change of the radiation dose delivered to the at least one volume element in accordance with the first dose distribution results in a fulfillment of the global dose constraint and to generate an instruction to change the radiation dose delivered to the identified at least one volume element.

11. The system as defined in claim 10, wherein a given fraction of a volume of the region of the patient absorbs a first radiation dose in accordance with the first dose distribution, wherein the global dose constraint requires that the radiation dose delivered to the fraction is larger than a specified second dose value and wherein the planning unit is configured to identify at least one volume element absorbing a radiation between the first and second radiation dose and to generate an instruction to change the radiation delivered to said at least one volume element.

12. A method for planning a radiation therapy treatment of a target structure in a region of a patient body, wherein radiation delivered to the region comprises a plurality of radiation contributions which are individually controllable on the basis of a treatment plan and wherein the method comprises:

obtaining a first treatment plan generated in accordance with values of parameters quantifying an amount of radiation provided by the radiation components and resulting in a first dose distribution in the region of the patient body, obtaining an instruction to change a radiation dose delivered to at least one volume element of the region according to the first dose distribution, directly calculating, for at least some of the radiation components, a change of the parameter value quantifying the amount of radiation provided by the radiation component on the basis of the contribution of the radiation component to the radiation dose delivered to the at least one volume element, calculating updated parameter values on the basis of the determined changes of the parameter values quantifying the amount of radiation provided by the radiation components, and determining a second treatment plan on the basis of the updated parameter values, wherein the parameter values quantifying the changes of the amount of radiation provided by the radiation components are bound to an upper and/or lower threshold and wherein the updated parameter values are calculated by iteratively adding the determined changes to the parameter values until a parameter value reaches the upper or lower threshold or until a dose distribution resulting from a treatment plan generated on the basis of the updated parameter values includes the changed dose of the at least one volume element.

13. Computer program comprising program code for instructing a computer device to perform a method as defined in claim 12 when the program code is executed in the computer device.

* * * * *